United States Patent [19]
Dinh

[11] Patent Number: 5,525,520
[45] Date of Patent: *Jun. 11, 1996

[54] PHOTO-ACTIVATED LUMINESCENCE SENSOR AND METHOD OF DETECTING TRICHLOROETHYLENE AND RELATED VOLATILE ORGANOCHLORIDE COMPOUNDS

[75] Inventor: Tuan V. Dinh, Knoxville, Tenn.

[73] Assignee: Martin Marietta Energy Systems, Inc., Oak Ridge, Tenn.

[*] Notice: The term of this patent shall not extend beyond the expiration date of Pat. No. 5,318,751.

[21] Appl. No.: 239,821

[22] Filed: May 9, 1994

Related U.S. Application Data

[60] Continuation-in-part of Ser. No. 109,759, Aug. 20, 1993, Pat. No. 5,318,751, which is a division of Ser. No. 937,685, Sep. 1, 1992, Pat. No. 5,272,089.

[51] Int. Cl.$^6$ .......................... G01N 33/18; G01N 21/64
[52] U.S. Cl. .......................... 436/126; 436/165; 436/172; 422/82.06; 422/82.07
[58] Field of Search .......................... 422/82.08, 82.06, 422/82.07; 436/126, 165, 172; 356/317, 318, 417

[56] References Cited

U.S. PATENT DOCUMENTS

| | | | |
|---|---|---|---|
| 5,028,395 | 7/1991 | Sebille et al. | 422/82.06 |
| 5,098,659 | 3/1992 | Yim et al. | 422/82.07 |
| 5,102,625 | 4/1992 | Meo | 422/82.07 |
| 5,119,463 | 6/1992 | Vurek et al. | 385/129 |
| 5,244,813 | 9/1993 | Walt et al. | 436/172 |
| 5,272,089 | 12/1993 | Vo-Dinh | 436/126 |
| 5,315,993 | 5/1994 | Alcala | 128/634 |
| 5,318,751 | 6/1994 | Vo-Dinh | 422/82.08 |

*Primary Examiner*—N. Bhat
*Attorney, Agent, or Firm*—Edward A. Pennington; Joseph A. Marasco; Harold W. Adams

[57] ABSTRACT

A sensor for detecting trichloroethylene and related volatile organochloride compounds uses a photo-activator that produces a photo-product complex with the contaminant. Characteristics of the light emitted from the complex will indicate the presence of the contaminant. A probe containing the photo-activator has an excitation light interface and a contaminant interface. One particular embodiment uses a porous membrane as the contaminant interface, so that the contaminant can migrate therethrough to the photo-activator and thereby form the complex.

19 Claims, 16 Drawing Sheets

PHOTO-ACTIVATED LUMINESCENCE SENSOR AND METHOD OF DETECTING TRICHLOROETHYLENE AND RELATED VOLATILE ORGANOCHLORIDE COMPOUNDS

This invention was made with Government support under contract DE-AC05-84OR21400 awarded by the U.S. Department of Energy to Martin Marietta Energy Systems, Inc. and the Government has certain rights in this invention.

RELATED CASES

This is a continuation-in-part of U.S. Ser. No. 08/109,759 filed Aug. 20, 1993, now issued as U.S Pat. No. 5,318,751 which is a divisional of U.S. Ser. No. 07/937,685 filed Sep. 1, 1992, now issued as U.S. Pat. No. 5,272,089.

FIELD OF THE INVENTION

The present invention relates generally to the screening of polychlorinated biphenyls (PCBs), and other related chlorinated compounds and, more specifically, to an enhanced photo-activated luminescence apparatus and optical methods for detecting trichloroethylene (TCE) and related volatile organochloride (VOC) compounds.

BACKGROUND OF THE INVENTION

Some chlorinated compounds, and in particular polychlorinated biphenyls (PCBs), TCE and related VOCs, have become a difficult environmental problem in that extremely minute levels are believed to-present a health risk. PCBs are a class of 209 discrete chemical compounds known as "congeners", in which one to ten chlorine atoms are attached to biphenyl. PCBs were widely used for several decades due to their superior properties of chemical and physical stability, heat resistance and high electrical resistance. They were used in heat transfer systems, hydraulics/lubricants, transformers, capacitors, plasticizer applications and petroleum additives, just to name a few.

The chemical and physical stability, viewed once as an asset of the PCB, is now recognized as an environmental liability since the PCBs do not readily degrade after disposal. Now the use of PCBs is regulated in the United States under the Toxic Substances Control Act (TSCA), PL 94-469 (U.S. Congress, 1976). This law is administered by the United States Environmental Protection Agency (EPA). Various rules and regulations have been promulgated concerning the production, use and disposal of PCBs. Other countries have passed similar legislation, making the control of PCB use and disposal a world-wide concern. While PCBs are presently not in wide scale production, it has been estimated that up to 1.3 billion pounds were produced world wide through the year 1976.

Given the chemical and physical stability of PCBs, it has been of increasing concern to regulators to monitor and screen samples of various types for PCB contamination. In general, while the specifics of the various national laws may differ, there is a common interest in determining the presence of PCBs in the environment. Determination techniques used in the past include gas chromatography, thin-layer chromatography, and high-performance liquid chromatography. Non-chromatographic techniques include nuclear magnetic resonance (NMR) spectrometry, infrared (IR) spectrometry, and immuno-assays.

"Screening" techniques are determinations characterized by speed and/or simplicity of methodology and apparatus. Typically, samples are screened where immediate analysis is needed, such as analysis in the field or during an incinerator trial burn to make sure that the PCBs are being destroyed. In general, the analysis of PCBs generally requires selectivity and sensitivity. Even after cleanup of a PCB-contaminated site, PCBs are usually at ultra-trace levels in field samples, mixed with other halocarbons, lipids, etc. The levels of PCBs typically found in water, soil, tissue, food, biota and other matrices of interest are in the parts per billion (ppb) range. Most current measurement techniques for PCBs require the aforementioned chromatographic separation techniques, which are not practical for routine analysis in the field. A review of the state of the art in PCB detection can be found in *Analytical Chemistry of PCBs* by M. D. Erickson (Butterworth Publishers, 1986). As described therein, packed column gas chromatography (GC), thin-layer chromatography (TLC), and high-performance liquid chromatography (HPLC) have been used to provide data on total PCB contents in samples. Packed column GC/ECD is the common method for quantification of PCBs such as AROCLORS made by the Monsanto Corporation in the American National Standards Institute (ANSI) procedures. In this procedure, the PCBs are quantified against an AROCLOR standard using the largest peak, or a secondary peak if necessary. Typically, this procedure was used to determine PCBs in sediments and soils.

If congener-specific determination is required, high-resolution gas chromatography (HRGC), which uses fused silica capillary columns, would be the preferred technique. High-resolution gas chromatography has been used for the analysis of PCBs in transformer fluids or waste oils.

Various mass spectrometry (MS) techniques, including electron impact MS, chemical ionization MS, coupled MS/MS, etc., have been used to analyze complex PCB samples. Methods involving perchlorination of the biphenyl ring of the PCB congeners have been used in the determination of PCBs. One limitation of the perchlorination approach is due to the fact that biphenyl can also be perchlorinated, thus leading to erroneously high blank levels.

Thin-layer chromatography (TLC) has been used in the analysis of PCBs. Detection using this technique has involved spraying the plates with silver nitrate followed by UV irradiation and fluorescence. See R. H. DeVos and E. W. Peet, *Bul. Envir. Contam. Toxicol.*, 6 (2), 164, 1971, for UV irradiation and J. Stahr, *Liq. Chromatogr.*, 7, 1393, 1984, for fluorescence. Two dimensional TLC has been used for PCB analysis, as described by N. V. Fehringer and J. E. Westfall in *J. Chromatogr.*, 57, 397, 1971. Photo-degradation of PCBs is a previously known process and fluorescence following UV excitation has been reported. See *The Chemistry of PCBs* by O. Hutzinger et al., R. E. Krieger Publishing Co., 1983.

Sensitized room temperature phosphorescence (RTP) has been used as the detection method for HPLC in PCB analysis. The method is based on the transfer of triplet energy of the analyte molecule (donor) to biacetyl (acceptor) and detection of sensitized RTP of biacetyl in liquid solutions. See T. Vo-Dinh, *Room Temperature Phosphorimetry For Chemical Analysis,* Wiley Publishers, 1984. The RTP method has recently been applied to PCB analysis.

Volatile organochloride (VOC) contaminants and co-contaminants at many industrial plants can be found at many industrial plants and federal sites. Many sites of the U.S.

Department of Energy (DOE) Are contaminated with mixtures of VOCs including trichloroethylene (TCE), perchloroethylene (PCE), and carbon tetrachloride. TCE has been widely used in the past as a common industrial solvent (degreasing agent). There has been a concern that TCE has contributed to the ozone depletion in the atmosphere. TCE is considered a significant environmental pollutant because laboratory bioassays have shown that its metabolized products can cause nephrotoxicity and nephrocarcinogenicity in laboratory animals. There is thus a strong need to develop a sensor that can detect liquid or vapor of TCE and related chlorinated compounds in-situ.

The analysis of TCE and chlorinated compounds (such as chlorinated solvents and volatile organochlorides) generally requires selectivity and sensitivity. TCE are usually at ultra-trace levels in field samples, mixed in with other halocarbons, hydrocarbons, etc. The levels of TCE typically found at industrial plants, DOE sites, or waste sites are in the part-per-billion (ppb) range to part-per-million (ppm) range.

There is a continuing need for a chemical sensor capable of detecting TCE and VOCs in liquid and vapor samples under field conditions.

SUMMARY OF THE INVENTION

An object of the present invention is to provide a method and apparatus for detecting TCE and VOCs in liquid and vapor samples under field conditions.

Another object of the present invention is to provide a method and apparatus for detecting TCE and VOCs which allows rapid decisions and reduces the need for either return visits to a site by a cleanup crew, or extensive and costly laboratory analyses of samples that contain no detectable levels of harmful compounds.

These and other objects of the invention are met by providing a method of testing for the presence of volatile organochlorides which includes the steps of exposing a probe containing a photo-activator to a sample suspected of containing an organochloride contaminant so that the organochloride, if present, and the photo-activator form a complex, irradiating the photo-activator with UV light to form a luminescence photo-product, exciting the photo-product, and detecting the luminescence of the luminescent photo-product.

Another aspect of the present invention is to provide a method to detect the complex using absorption, reflection, scattering, and color change techniques, in addition to luminescence.

Other objects, advantages and salient features of the invention will become apparent from the following detailed description, which, taken in conjunction with the annexed drawings, discloses preferred embodiments of the invention.

DETAILED DESCRIPTION OF THE PREFERRED EMBODIMENT

Figure 1:
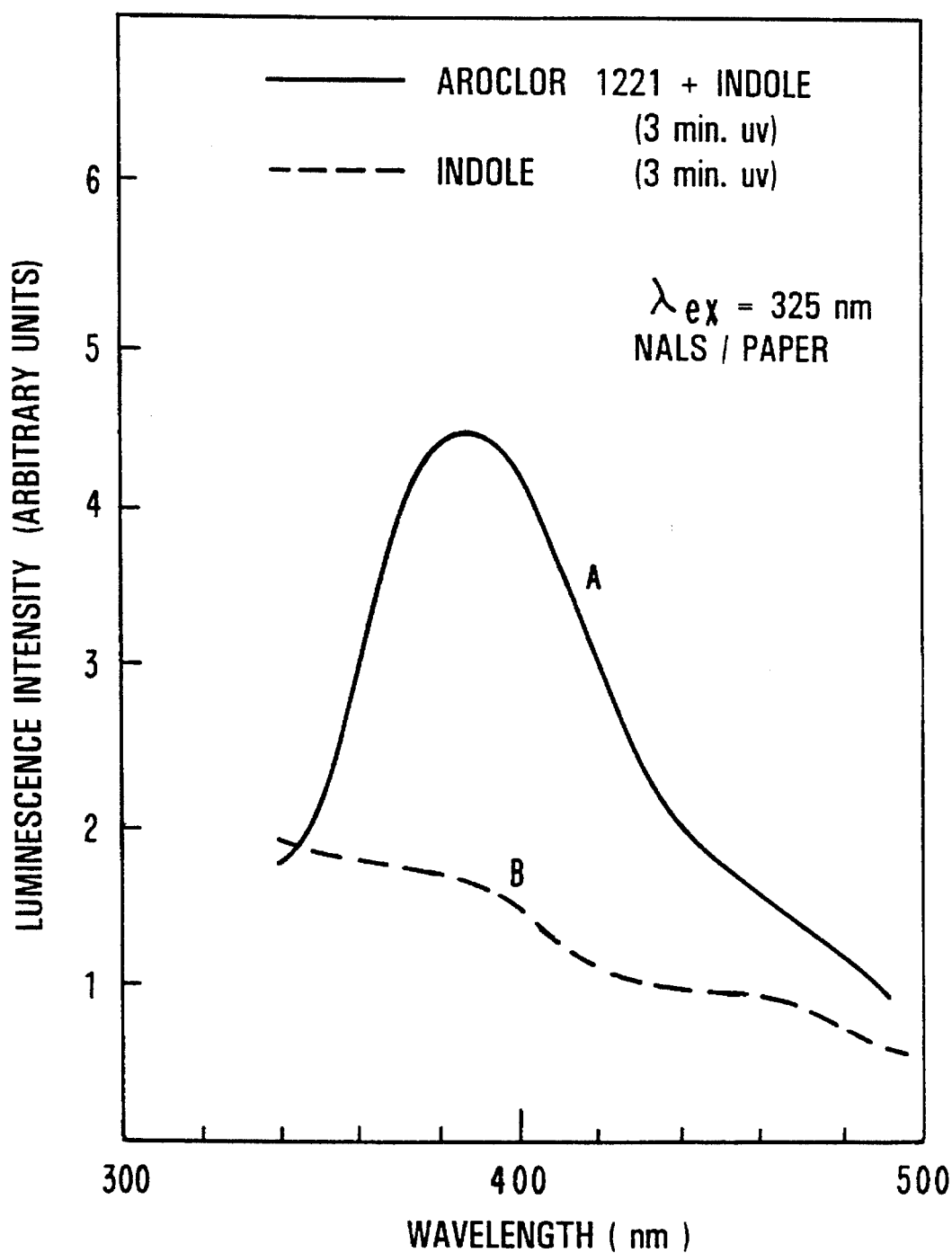
FIG. 1 is a graph showing luminescence spectra of indole/PCB (Aroclor 1221) photo-product as curve "A", and of idole alone as curve "B", using a 325-nm excitation source following 3 minute photo-activation at 254 nm.

The techniques described in the related applications are based primarily on a three-step procedure which combines several processes that are integrated to provide a relatively simple and inexpensive screening of chlorinated compounds such as PCBs.

As a first step, a sample which is to be tested or screened for the presence of chlorinated compounds such as PCBs is treated with a photo-activator. Suitable photo-activators include indole, diphenylamine (DPA), pyrrole, and imidazole. The photo-activator and PCBs present in the sample form a complex. The present invention encompasses the discovery that in the presence of a suitable photo-activator, illumination of PCBs with ultraviolet (UV) light (at wavelength $\lambda_1$) results in the generation of a luminescent photo-product of the photo-activator/PCB complex. The photo-product complex is then excited with a light source at a different wavelength ($\lambda_2$) than the first illumination. The luminescence product of the second illumination step is detected at still another excitation wavelength ($\lambda_3$), $\lambda_3$ being $>\lambda_2$. In general, $\lambda_3>\lambda_2$. There is no specific relationship between $\lambda_1$ and $\lambda_2$, although experiential data shows that $\lambda_2>\lambda_1$. $\lambda_1$ is UV light of sufficient energy to form the photo-product, and $\lambda_2$ is UV light of sufficient energy to excite the photo-product into an excited electronic state leading to subsequent fluorescence at $\lambda_3$.

A possible process in photo-chemical reaction is reductive dechlorination of the PCBs which involves C—Cl bond cleavage to produce biphenyl free radical species. Formation of a luminescent product is likely due to interaction of the biphenyl free radical species and/or of the chlorine ions (photolyzed from PCB under UV irradiation) with the photo-activator. Since Aroclors are complex mixtures of PCBs, the exact photo-chemical reactions and kinetics for each congener cannot be described in detail.

Photo-chemical degradation of PCBs via UV irradiation is determined by the degree of chlorination and the positions of chlorine substitution in the biphenyl nucleus. This photo-chemical reaction involving the photo-activator increases with time as indicated by the increase in luminescence intensity, which reaches a maximum within 3–7 minutes (depending on the type of Aroclor).

The following reaction mechanisms may be involved for a complex of PCB and either indole or DPA:
(1) PCB+Ph+hv1→(PCB)'+Ph-c
(2) Ph-c+hv2→(Ph-c)*
(3) (Ph-c)*→Ph-c+hv3
where:
hv1=UV irradiation for photo-activation (e.g. 254 nm)
hv2=excitation of the complex Ph-c (e.g. 325 or 354 nm)
hv3=luminescence from the excited state (Ph-c)* (405 nm)
(PCB)'=photo-product of PCB following UV irradiation with hv1
Ph=photo-activator (e.g., indole, DPA)
Ph-c=ground state of photo-activator product complex following interaction with PCB and hv1 irradiation
(Ph-c)*=excited electronic state of Ph-c In the above, step (1) is the photo-activation step, step (2) is the excitation of the photo-product step, and step (3) is the detection of luminescence step. The luminescence from (Ph-c)* appeared during experimentation to be fluorescence (from an excited single state) since the emission decay time was very fast, although involvement of an excited triplet state process and/or phosphorescence emission should not be ruled out and may occur under certain specific conditions.

EXAMPLE 1—Indole Photo-activator

Indole alone exhibits no luminescence when excitation is used at 325 nm since it absorbs at higher energies (i.e., shorter wavelengths). PCBs do not show luminescence under similar excitation conditions. However, when PCBs are in the presence of indole, UV irradiation of the mixture PCB/indole using 254 nm (hv1) light, a photo-product complex Ph-c is formed. When this photo-product complex Ph-c is excited by hv2 (e.g. 325 nm) excitation (step 2), a luminescence emission with a maximum peak at approximately 390 nm can be detected. It is noteworthy that UV irradiation of indole or PCBs separately do not produce the 390 nm luminescence. The luminescence of the photo-product illustrate in FIG. 1 can be used to identify and quantify PCBs.

FIG. 1 represents a luminescence spectra generated for a PCB Aroclor 1221+indole, which was initially excited with a UV light source at an excitation wavelength of 254 nm, followed by a second excitation at an excitation wavelength ($\lambda$ex) of=325 nm for 3 minutes. The sample containing Aroclor 1221 and indole was placed on a paper substrate treated with sodium lauryl sulphate (NaLS). The graph of FIG. 1 was produced by an X-Y plotter of an analog recording system of a luminescence spectrometer. The spectrometer will be described in more detail below. Graph "A" shows luminescence of the indole/PCB photo-product, while graph "B" shows luminescence of only indole.

EXAMPLE 2—DPA photo-activator

Figure 2:
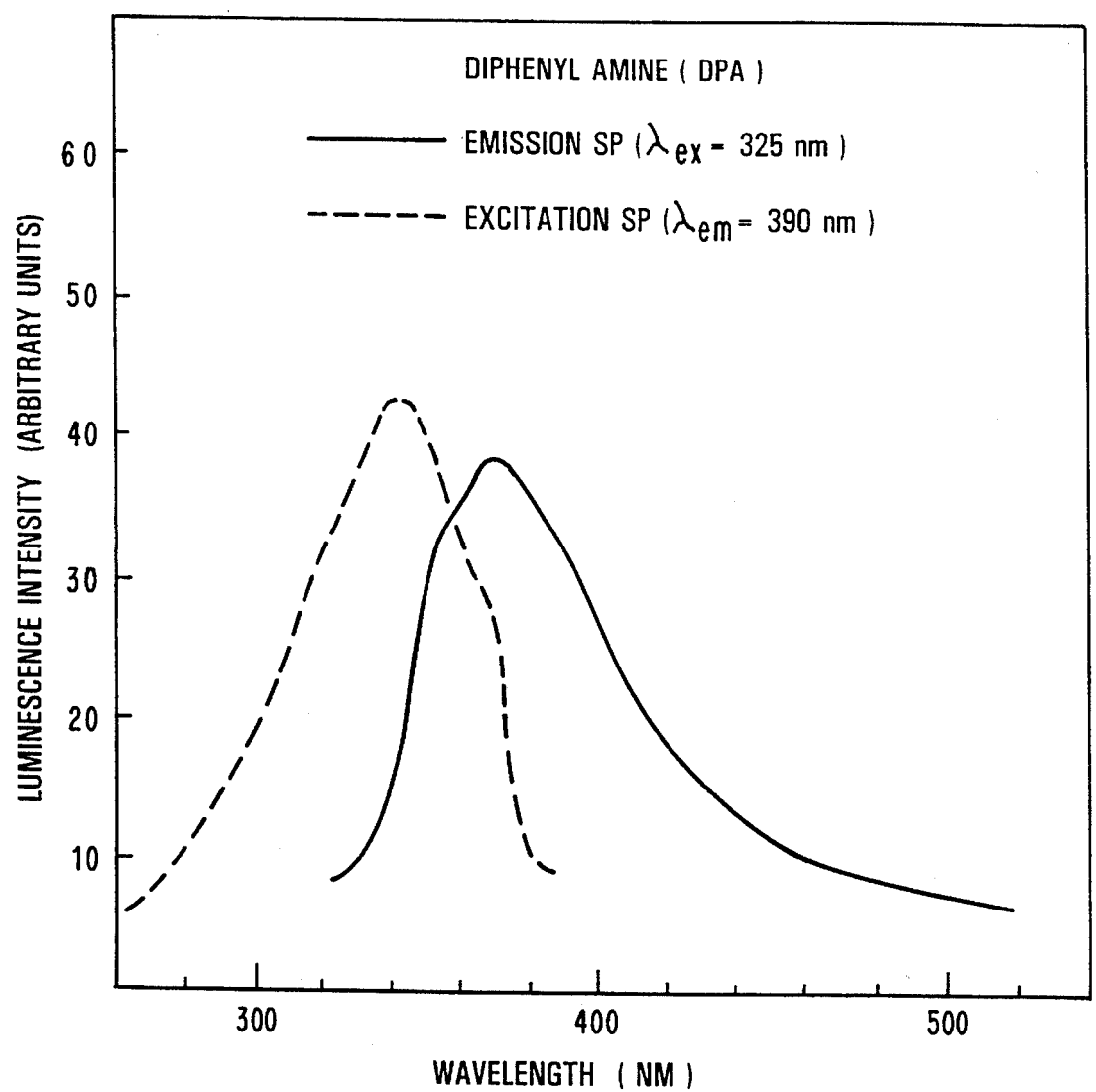
FIG. 2 is a graph showing luminescence spectra of diphenylamine (DPA)
Figure 3A:
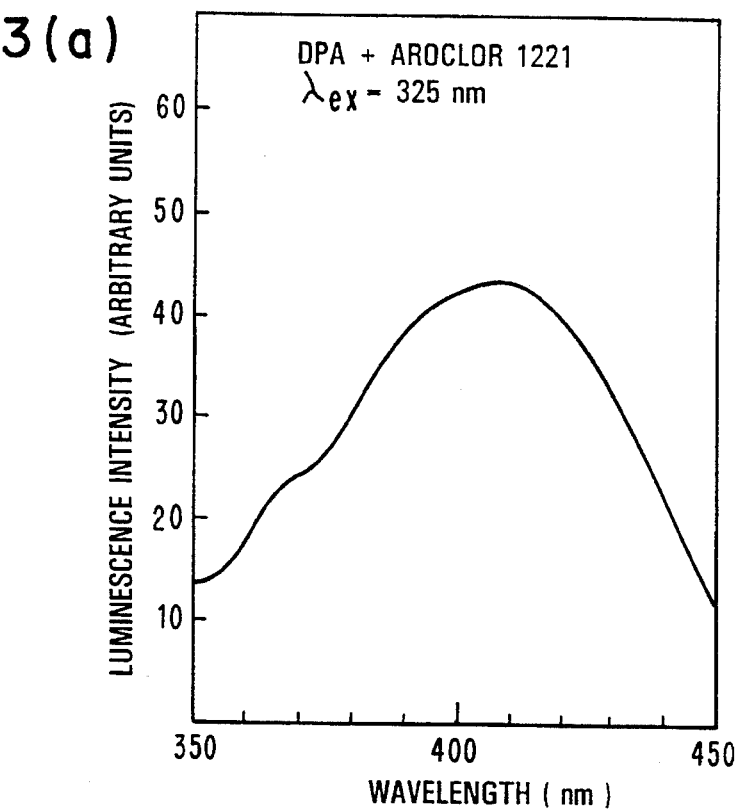
FIGS. 3(a) and 3(b) are graphs showing luminescence spectra of DPA and PCB complexes, with excitation at 325 nm and 355 nm, respectively.

As shown in FIG. 2, the photo-activator DPA exhibits luminescence having a maximum peak at approximately 365 nm. Following UV irradiation (hv1) of the mixture of PCB and DPA at 254 nm (hv1) with a handheld lamp (Model UVGL-58, UVP, Sam Gabriel, Calif.) the photo-product Ph-c is formed. This complex Ph-c exhibits a broad-band luminescence at approximately 405 nm, as seen in FIGS. 3(a) and (b), when it is subjected to hv2 excitation at<360 nm (e.g., 325 nm or 354 nm). The optimum UV irradiation (254 nm) time is 3–5 minutes. The 254 nm line of the handheld lamp was used because of its availability and this excitation wavelength can photo-induce PCBs, which have absorption up to 280 nm. Use of another wavelength (e.g., <254 nm) is also possible as long as it is capable to photo-activate the PCB-DPA complex.

Figure 3B:
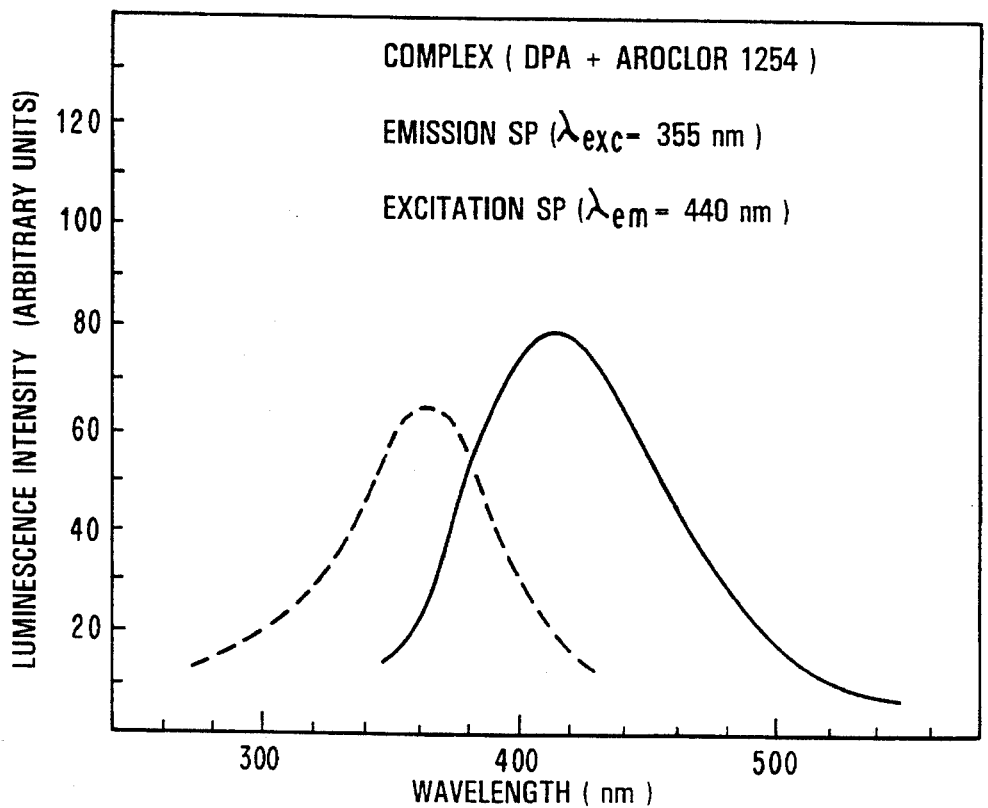

For a sample containing only DPA and no PCB, a strong emission peak at 365 nm was generated, as seen in FIG. 2. This emission peak is associated with DPA luminescence. When PCB is added to DPA and the resulting mixture is subjected to 254 nm UV irradiation, the luminescence peak of DPA at 365 nm decreases whereas a new luminescence emission band at 405 nm (hv3) appears. The 405 nm luminescence band is associated with the photo-product complex DPA-c since it is proportional to the amount of PCB added to the DPA sample. As shown in FIGS. 3(a) and 3(b), a decrease of the 365 nm band (associated with DPA luminescence) with a simultaneous increase of the 405 nm emission (associated with the complex DPA-c) manifests the presence of PCB.

If the excitation occurs at 354 nm instead of 325 nm, the emission band at 405 nm is observed with minimal interference from the 365 nm band. This is due to the fact that the 354 nm excitation masks the DPA emission at 365 nm. This is also due to the fact that DPA is not excited or weakly excited by the 354 nm excitation light.

In the foregoing examples, DPA and indole were used to illustrate the capability of the present invention to detect the presence of PCBs in samples. It is also possible to determine the chlorine content of the PCB mixture contained in the sample. According to the present invention, the luminescence intensity at, for example, hv3=405 nm, is due to the reaction PCB/hv1/DPA. This intensity has been found to be proportional to the number of total chlorine in the PCBs. This is consistent with the photo-chemical dechlorination of PCBs. To demonstrate, an example is given below involving a given PCB sample with a number "n" proportional to the total of chlorine content. This feature confirms that the photo-chemical reaction involves dechlorination PCBs:
PCB (with n Cl atoms)+n hv1→PCB'+n Cl (4)
n Cl+n DPA→n (DPA-c) (5)
n (DPA-c)+n hv2→n (DPA-c)* (6)
n (DPA-c)*→n (DPA-c)+n hv3 (luminescence) (7)

Equation 7 above indicates that the luminescence intensity (hv3) is proportional to n, the number of total chlorine atoms in PCB samples. For example, with Aroclor 1221, n=21; with Aroclor 1254, n=54; with Aroclor 1260, n=60, etc. With a sample containing varying amounts of different Aroclors, e.g., 10% Aroclor 1221, 60% Aroclor 1254, and 30% Aroclor 1260, the number n is equal to 2.1 (10% of 21)+32.4 (60% of 54)+18 (30% of 60)=52.5. It is therefore possible to quantify the total chlorine content of a complex sample having different amounts of Aroclors by measuring the intensity of the emission band at 405 nm. The quantitative determination of total chlorine content of several mixtures of different Aroclors is shown in Table 1 as follows:

TABLE 1

QUANTITATIVE DETERMINATION OF TOTAL CHLORINE CONTENT IN COMPLEX MIXTURE OF PCB (AROCLOR)

| MIXTURE OF AROCLOR (*) | EXPERIMENTAL (% Cl Content) | THEORETICAL (% Cl) |
|---|---|---|
| With DPA as the Photo-Activator | | |
| 1262 (5 μL) + 1254 (3 μL) + 1242 (2 μL) | 52 | 54.6 |
| 1260 (6 μL) + 1248 (3 μL) + 1242 (1 μL) | 52 | 54.6 |
| 1254 (2 μL) + 1242 (3 μL) + 1248 (5 μL) | 43 | 47.4 |
| 1221 (3 μL) + 1242 (2 μL) | 30 | 29.4 |
| With Indole as the Photo-Activator | | |
| 1221 (6 μL) + 1232 (4 μL) | 28 | 25.4 |
| 1248 (2 μL) + 1260 (3 μL) + 1221 (5 μL) | 39 | 38.1 |

(*) Aroclor No. sample is designated by 4-digit number

TABLE 2

LIMIT OF OPTICAL DETECTION (LOD) USING THE PRESENT ENHANCE LUMINESCENCE TECHNIQUE WITH NALS AND TiO2 TREATMENT

| ANALYTE | LOD (PART-PER-BILLION) |
|---|---|
| Aroclor 1121 | 4.2 |
| Aroclor 1242 | 2.3 |
| Aroclor 1248 | 2.3 |
| Aroclor 1254 | 2.5 |
| Aroclor 1260 | 3.0 |

Figure 4:
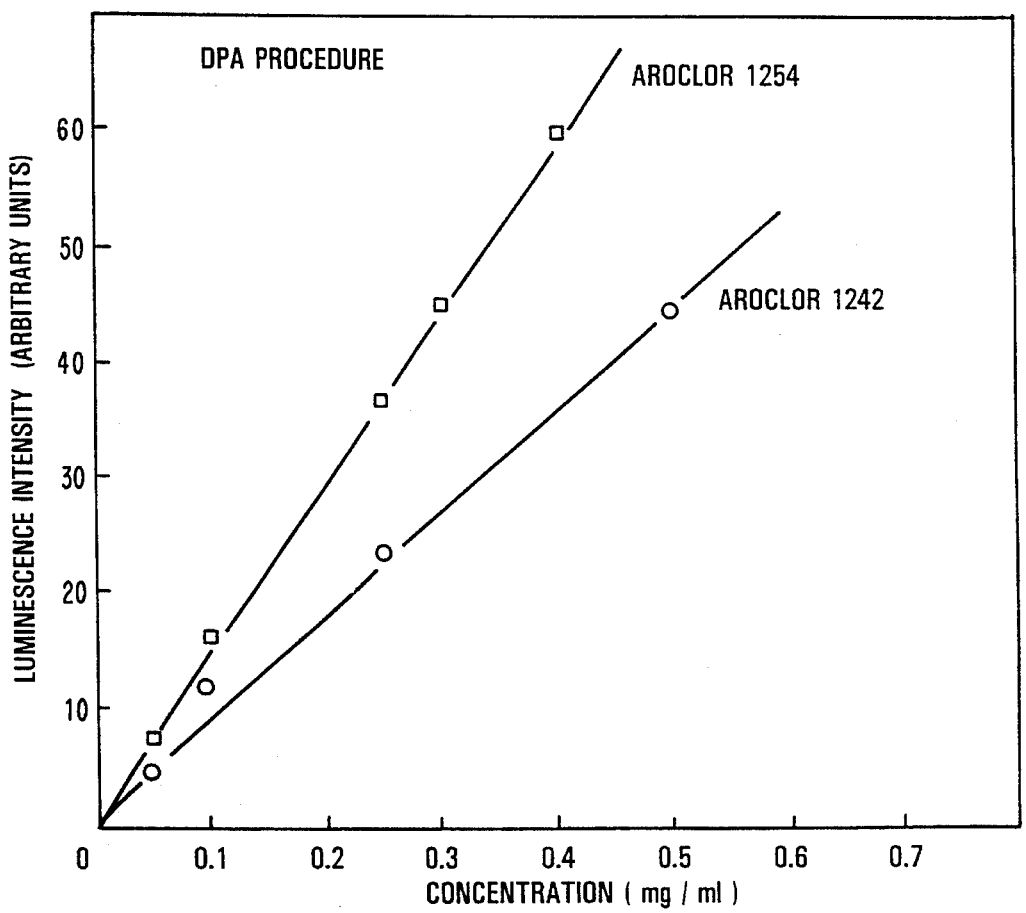
FIG. 4 is a graph showing calibration curves for Aroclor 1254 and Aroclor 1242.
Figure 5:
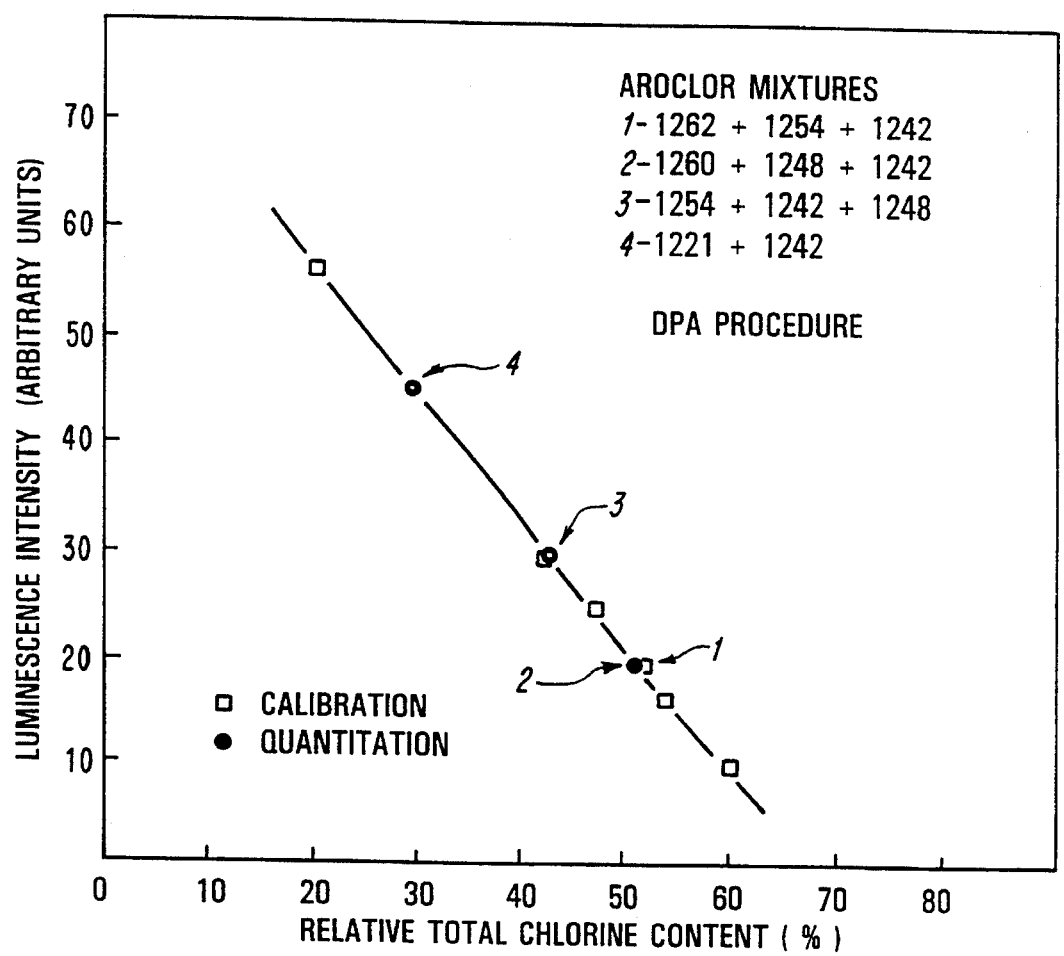
FIG. 5 is a graph showing the relationship between luminescence intensity and total chlorine content using the DPA photo-activation.
Figure 6:
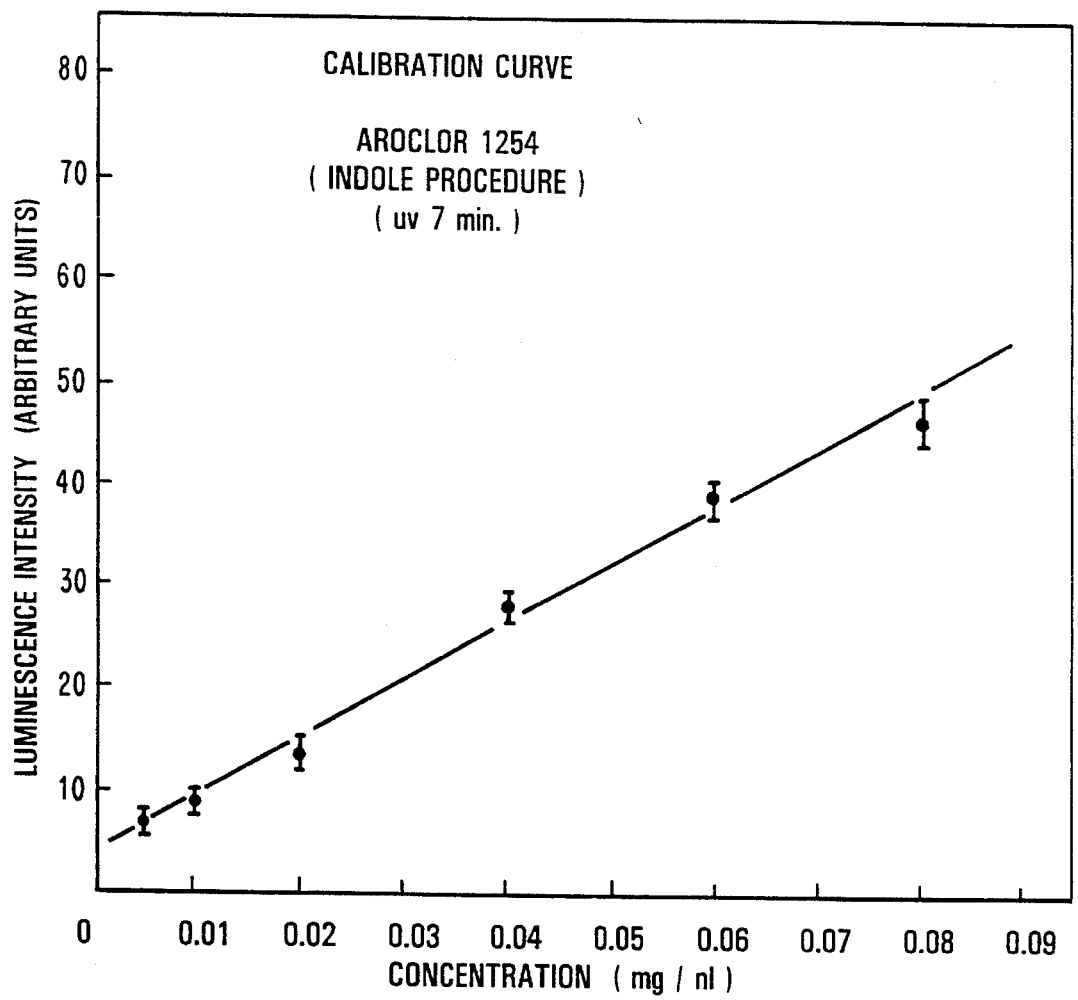
FIG. 6 is a graph of a calibration curve of the PCB Aroclor 1254 using the indole photo-activator.
Figure 7:
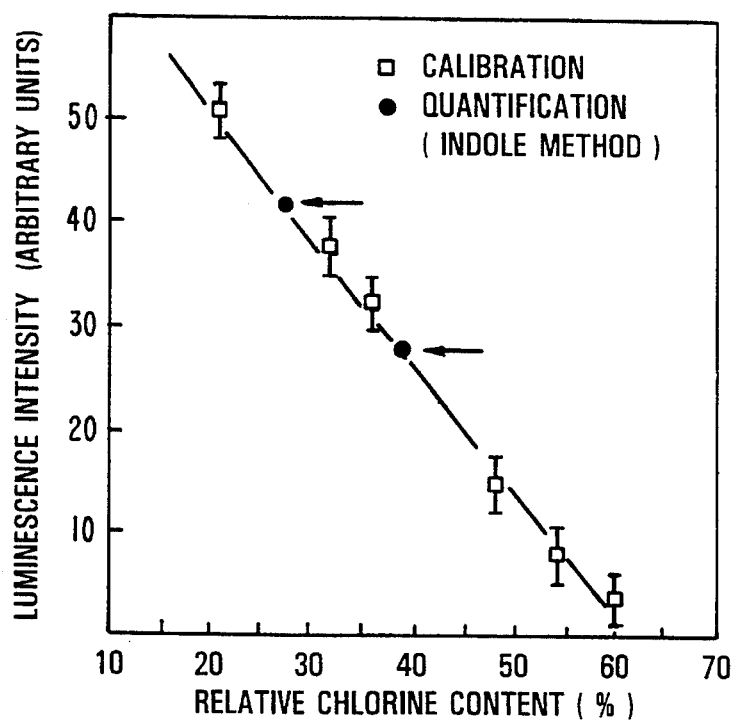
FIG. 7 is a graph used to determine chlorine content of a sample using the indole enhanced photo-activated luminescence technique of the present invention.

FIG. 4 shows examples of calibration curves for Aroclors 1242 and 1254. The limits of detection for Aroclors 1221, 1254, and 1260 are 4, 2.5, and 3 ppb, respectively. The relationship between luminescence intensity and the chlorine content of the complex mixtures is illustrated in FIG. 5. The total chlorine content of Aroclors discussed in Table 1 is determined with the quantitation data in FIG. 5. Similar results using indole as the photo-activator are illustrated in FIG. 6 (calibration curve of Aroclor 1254) and FIG. 7 (determination of chlorine content).

One aspect of the techniques described in the related applications is the treatment of the substrate to achieve an enhanced photo-activation and detection. This treatment was mentioned briefly above as a surfactant applied to the surface of the substrate. Without the substrate treatment procedures, the sensitivity and reproducibility may not be sufficient for quantitative determination of chlorine content of PCB. Two substrate treatment procedures, involving surfactants and $TiO_2$, semiconductor particles, are described below.

In one embodiment of the parent invention, the substrate is treated with sodium lauryl sulfate (NaLS). Other surfactants, such as CTAB, the nonionic surfactant ethylene oxide propylene oxide condensate Genpol-20, cyclodextrins, micellar systems, etc., could be used as well. In the surfactant media, the sensitivity, stability, and selectivity of photo-physical reactions are improved and photo-chemical products and complexes are generally more stable than when formed in the absence of surfactants. The presence of NaLS improves the efficiency of the photo-chemical interactions between PCB, S, and light. Surfactants have several unique properties which should facilitate analytical measurements using photo-luminescence. For example, they have the ability to solubilize and concentrate reactant (DPA/analyte) and they can alter quantum efficiencies, chemical and photo-physical pathways and rates. As a result of the surfactants, an increase in the luminescence intensity of each PCB test is expected and has been observed using NaLS. It is thus possible to lower the detection limits of the assay and achieve greater sensitivity. This is a particular advantage achieved by the present invention, given that PCBs need to be screened on a ppb basis. Additionally, surfactants are optically transparent, stable, photo-chemically inactive, inexpensive, and relatively nontoxic. The use of surfactants is an important step since it makes the luminescence technique of the present invention more sensitive and more reproducible, thus allowing quantification of the chlorine content. According to one particular embodiment of the present invention, the intensity of (ph-c)* is maximum for an NaLS concentration of 1% on the substrate.

The substrate may also be treated with the photo-activator, to form a complex with the sample placed on the substrate. Thus, the photo-activator can be either mixed into the sample or placed on (or in) the substrate, or both.

Figure 8:
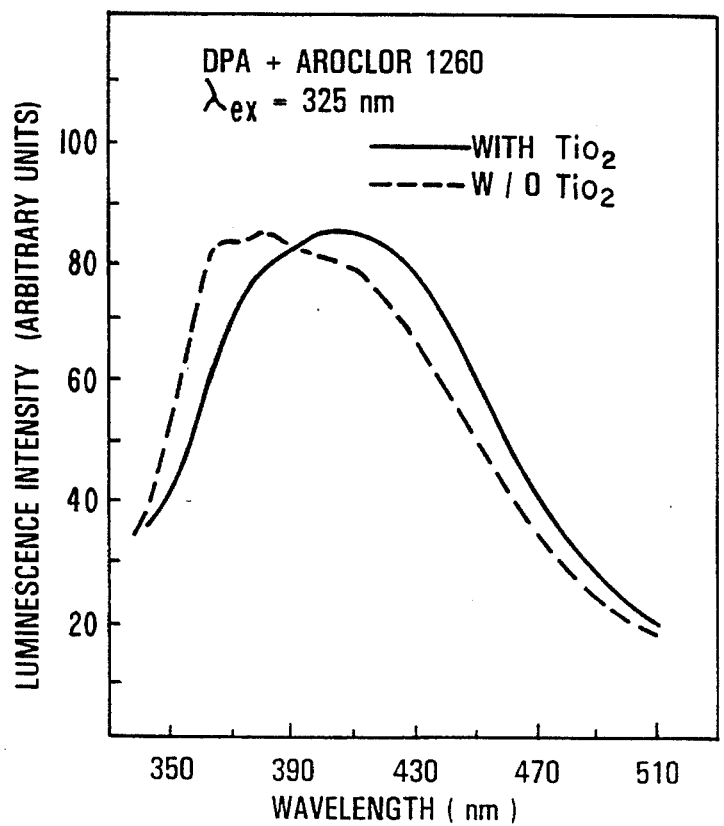
FIG. 8 is a graph showing luminescence spectra for a DPA and PCB complex with and without a treatment on the substrate using titanium oxide coating.

Another treatment of the substrate according to the parent applications involves the use of semiconductor particles. Semiconductors, dispersed as colloids, powders, crystalline films, or single crystals, have been effectively employed for driving charge separation processes, redox reactions of both organic and inorganic substrates. In the present invention, treating the substrate with can enhance the formation of the luminescent DPA-PCB complex. This might be due to an increase in the speed of the DPA-PCB complex formation in the presence of. FIG. 8 shows that with treatment the emission of DPA at 365 nm decreases whereas the emission at 405 nm (from DPA-c) increases, thus reflecting a more efficient formation of the DPA-c photo-product of interest.

Figure 9:
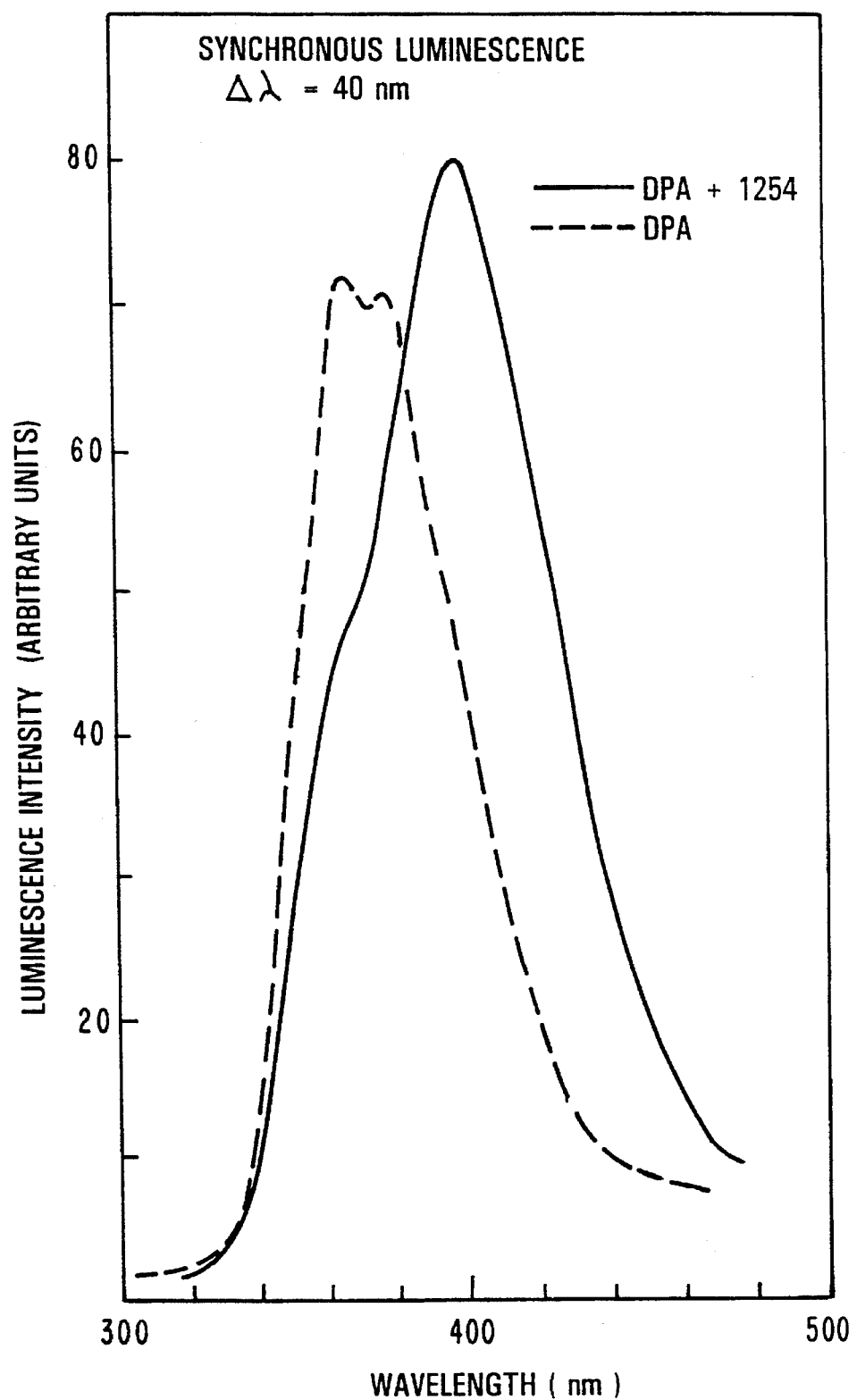
FIG. 9 is a graph showing synchronous luminescence spectra of DPA and DPA-c.

The selectivity of the present enhanced photo-activated luminescence technique can be further improved by using the synchronous excitation or synchronous luminescence (SL) method. The synchronous methodology consists of scanning both excitation and emission wavelengths simultaneously, by keeping a constant wavelength interval between them. The SL technique has been described by T. Vo-Dinh in *Modern Fluorescence Spectroscopy*, E. L. Wehry, Ed., Plenum Press, New York, 1981), which is incorporated herein by reference. FIG. 9 shows the SL spectra of DPA and DPA-c using a wavelength interval of 40 nm. The SL technique narrows the emission bands of DPA and DPA-c, thus permitting a better spectral separation of these two species when both are present.

Figure 10:
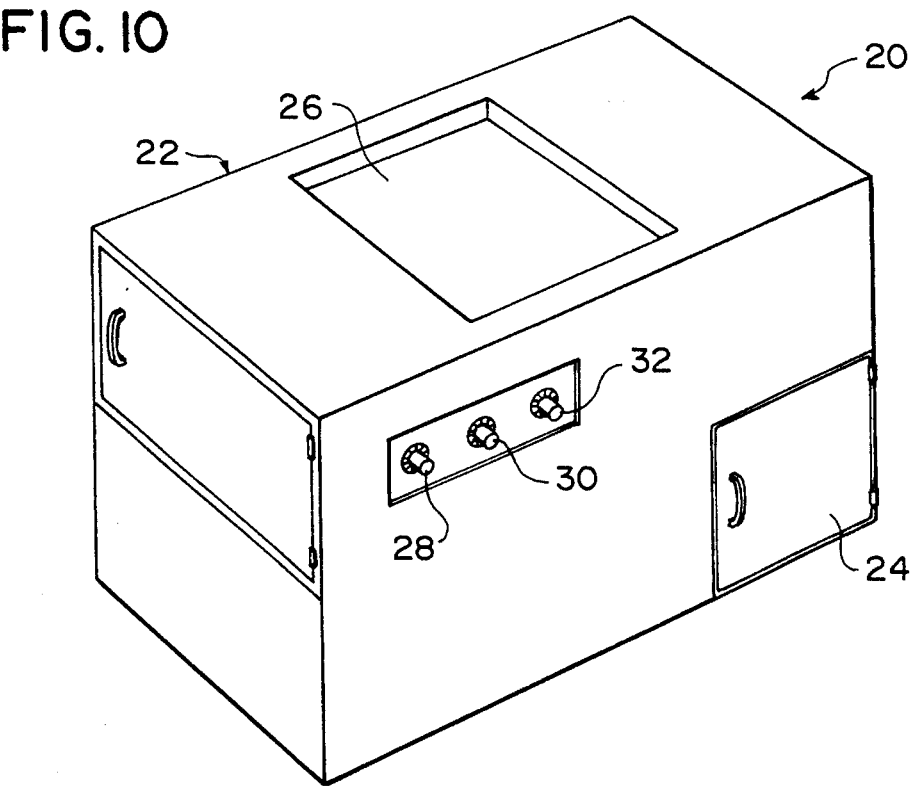
FIG. 10 is a perspective view of a portable field instrument for screening samples for PCBs and related chlorinated compounds according to the present invention.
Figure 11:
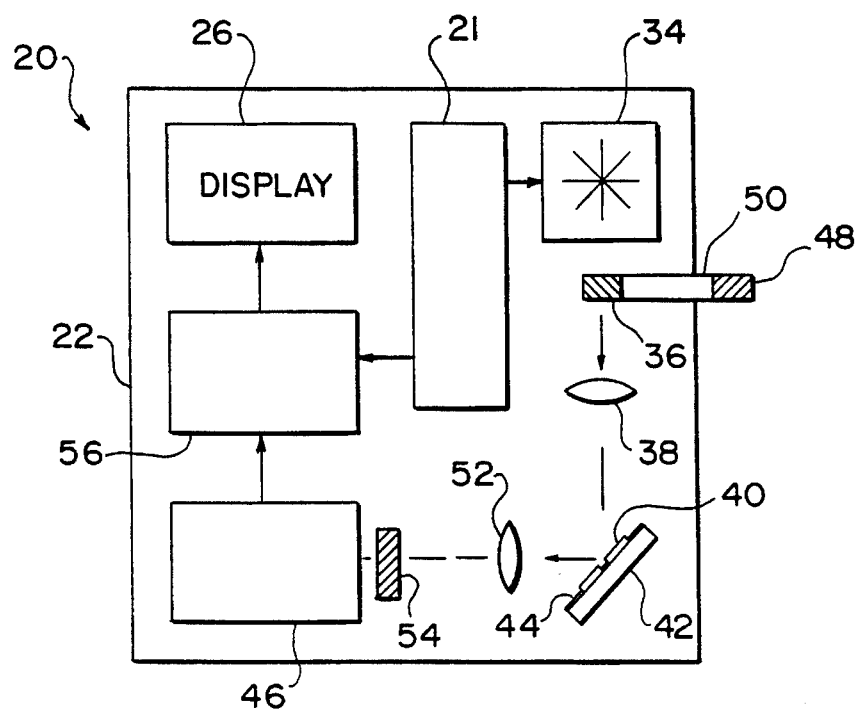
FIG. 11 is a schematic view of the portable field instrument of FIG. 10.

Due to the relative simplicity of the parent techniques, a portable field instrument can be used in which the entire sampling/irradiation/detection protocol for the inventive technique are integrated. Referring to FIGS. 10 and 11, a portable field instrument 20 for testing samples for chlorinated compounds such as PCBs includes a housing 22 having an overall size and shape suitable for carrying in an instrument carrying case (not shown). The housing 22 has a sample door 24 which can be opened to gain access to a sample holder (not shown in FIG. 10). The field instrument 20 includes a digital display 26 or other suitable indicator means so that when the technician makes a field analysis of a sample of material potentially containing PCBs, for example, the results of the analysis can be viewed immediately.

Preferably, the instrument 20 has a self-contained battery power supply 21 so as to facilitate remote site screening. A power on/off switch 28, a timer dial 30, and a light source wavelength selector 32 are provided on the housing 22 for easy access by the technician. The timer dial switch 30 can be programmed to select, adjust, and synchronize the photo-activation time, excitation time, and detection time automatically.

Referring to FIG. 11, a UV light source 34 disposed within the housing 22 radiates light at a wavelength determined by an optical filter 36. The optical filter 36 provides that the light passing therethrough is at the desired, predetermined wavelength. In the examples described above, this would correspond to hv1 or 254 nm so as to provide the necessary photo-activation of the PCB/photo-activator. A lens 38 focuses the UV light onto the sample 40 which is mounted on the sample holder 42. A paper sheet 44 mounted on the sample holder 42 is preferably treated with a surfactant as described above to enhance the sensitivity of the screening technique.

Irradiating UV light at 254 nm on the sample 40 for a predetermined period of time forms a photo-product complex from a mixture of PCB and photo-activator, such as indole, contained in the sample 40. The photo-product complex is then excited by UV light at another wavelength of, for example, 325 nm. This causes a luminescence emission with a maximum peak at approximately 390 nm which is detected by a photo-detector 46. In order to produce excitation at the second wavelength, the first optical filter 36 is replaced by a second optical filter 48 which changes the wavelength of the light irradiating from the source 34 to a second wavelength, such as 325 nm. Both optical filters 36 and 48 may be contained in a holder 50 which is rotated or translated to position the desired one of the two filters in the optical path of the light source 34. The luminescence of the sample, after excitation at the second wavelength, is focused through a lens 52 and passes through a third optical filter before being detected by the photo-detector 46. The detected peak wavelength corresponds to hv3 in the examples described above.

Figure 13:
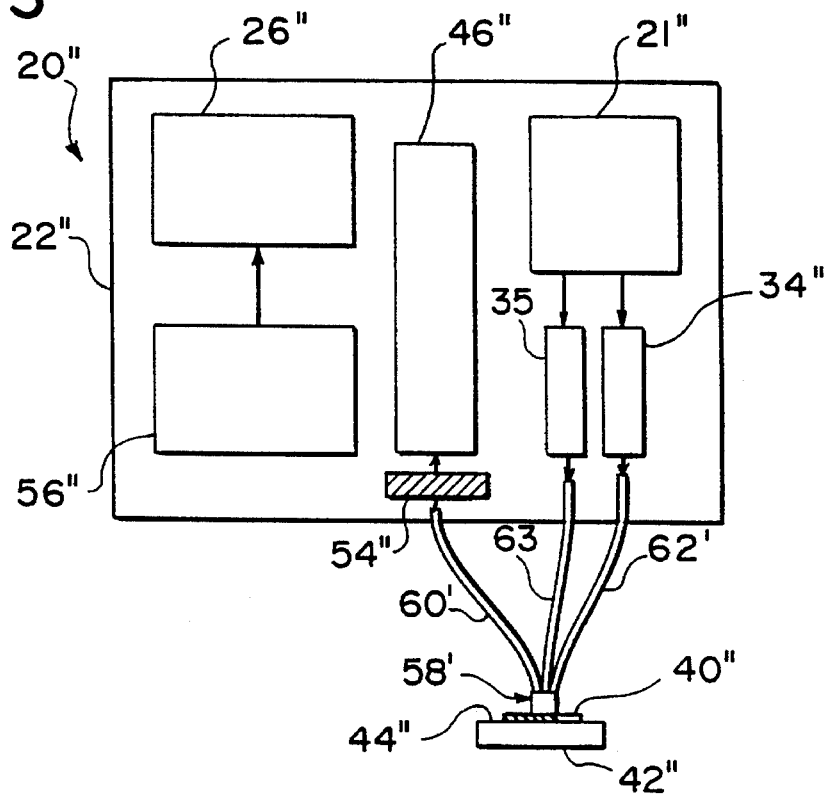
FIG. 13 is a schematic view of a variation of the portable field instrument of FIG. 12.

In another embodiment, illustrated in FIG. 13 and described more fully below, two different light sources are housed in the housing 22 and a mechanical shutter or electrical gating system allow photo-activation and excitation of the sample 40. The system can also be programmed to set and synchronize the photo-activation, excitation and detection cycles automatically.

An electrical signal indicative of the detected luminescence is delivered to a processor 56 which processes the photo-detector signal into an appropriate form. For example, the processor 56 could be programmed to output signals to the digital display 26 so as to give the operator either a reading of the spectra, the peak wavelength, or simply a "positive" or "negative" indication of PCB contained in the sample. Moreover, the processor 56 can be equipped with memory so that data can be gathered in the field and downloaded to a central computer for further analysis. Additional display devices can be provided on the portable instrument 20, including an X-Y plotter for providing a printout of the detected spectra.

Figure 12:
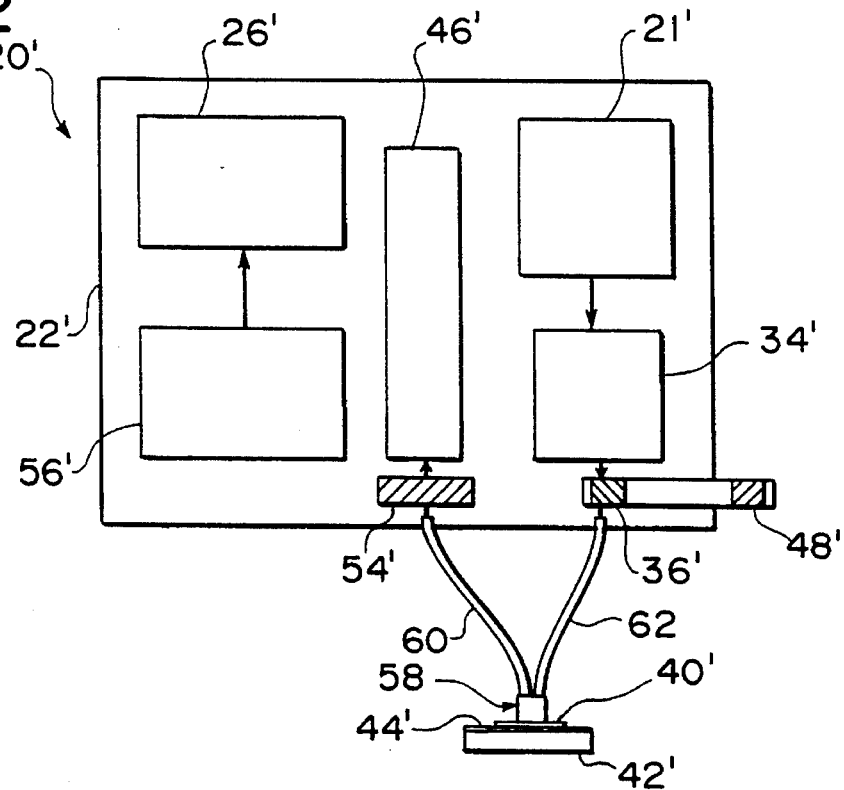
FIG. 12 is a schematic view of a variation of the portable field instrument of FIG. 10.

A variation of the embodiment of FIGS. 10 and 11 is seen in FIG. 12, in which like parts are of the same number, but primed, as in the prior embodiment. The difference lies in the fact that the sample holder 42' is external of the housing 22'. Samples 40' are screened by using a fiber optic probe 58 coupled to the housing 22' by two fiber optics 60 and 62. The fiber optic 62 delivers the UV light to the sample 40' after passing successively through filters 36' and 48'. Luminescence following the second excitation step is delivered through the fiber optic 60 to the photo-detector 46' after passing through the hv3 filter 54'.

In either embodiment, the use of two separate light sources, each having a different UV wavelength selected to accomplish the three-step method of the present invention can be used instead of a single source with two optical filters. In the interest of saving space, the single source with two optical filters is preferred. The hv1 filter 36, 36' provides photo-activation, and the hv2 filter 48, 48' provides excitation to a luminescence state. The hv3 filter 54, 54' is needed in either embodiment for luminescence detection. An example of two separate U.V. sources 34" and 35 is shown in FIG. 13 respectively optically coupled to fiber optics 62' and 63.

In order to improve the analysis, the present method can be combined with a rapid thin-layer chromatography (TLC) or paper chromatography (PC) separation that can be performed in situ on the sample substrate spotted with PCB samples. Since the present method involves luminescence on filter paper substrate, it is compatible with any chromatographic separations performed on the same substrate. This integrated procedure is simple, rapid and can improve the selectivity of the spot test since interfering compounds can be chromatographically separated from the PCBs. Also, different types of PCBs can also be chromatographically separated to a certain extent prior to luminescence detection.

Different types of Aroclors exhibit a maximum luminescence signal after different UV irradiation times. It is possible according to the present invention to use this difference in UV irradiation time in order to selectively increase the luminescence of a certain photo-product due to a certain type of Aroclors.

Methodology Specific To VOCs and TCEs

The techniques and apparatuses described above may not be used for VOCs since VOCs are volatile compounds and do not remain on the substrate for detection.

According to a method developed for detecting volatile compounds, a TCE sample is illuminated with UV light in the presence of a photo-activator, Ph. This results in formation of a luminescent photoproduct (photo-activator-TCE complex). A preferred photo-activator is diphenylamine (DPA), although other photo-activators could be used.

Formation of a luminescent product may be due to interaction of the chlorine ions (photolyzed from TCE under UV irradiation) with the photo-activator). This photochemical reaction involving the photo-activator increases with time as indicated by the increase in luminescence intensity, which reaches a maximum within ten to twenty minutes. The following reaction mechanisms may be involved:

(a) Formation of Photo-product (PhC) TCE+DPA+hv1→PhC
(b) Excitation of Photo-product PhC+hv2→(PhC)*
(c) Luminescence Detection (PhC)*→PhC+hv3 where:
hv1=UV irradiation for photo-activation
hv2=excitation of the complex PhC
hv3=luminescence from the excited state (PhC)*
TCE=trichloroethylene
Ph=photo-activator (e.g., DPA)
PhC=ground state of photo-activator/TCE product complex following hv1 irradiation,
and
PhC*=excited electronic state of PhC The luminescence from PhC* appears to be fluorescence (from an excited singlet state) since the emission decay time is very fast, although involvement of an excited triplet state process and/or phosphorescence emission cannot be ruled out and may occur under certain specific conditions.

Apparatus Specific To VOCs and TCEs

Figure 14:
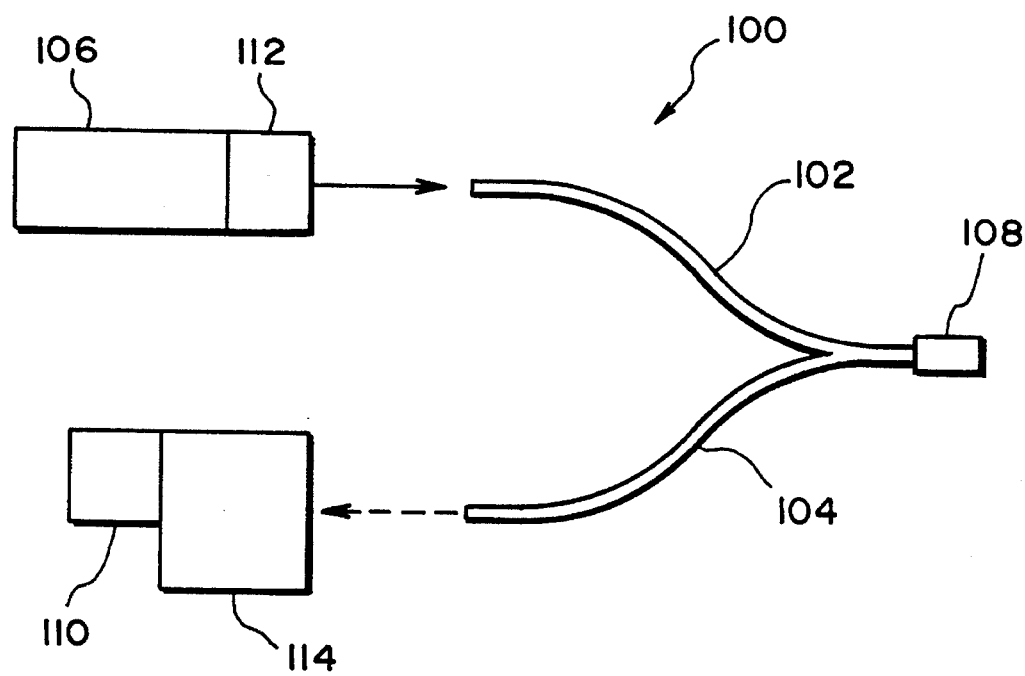
FIG. 14 is a schematic view of a photo-luminescence sensor according to a preferred embodiment of the present invention.

Referring to FIG. 14, a photo-activated luminescence sensor 100 includes a bifurcated fiberoptic system having first and second optical fibers 102 and 104. The first fiber 102 carries excitation radiation from a light source 106 to a probe 108, while the second fiber 104 transmits the emission from the probe 108 to a photodetector 110. Dispersive devices 112 and 114 are associated with the light source 106 and the photodetector 110, respectively.

Figure 15:
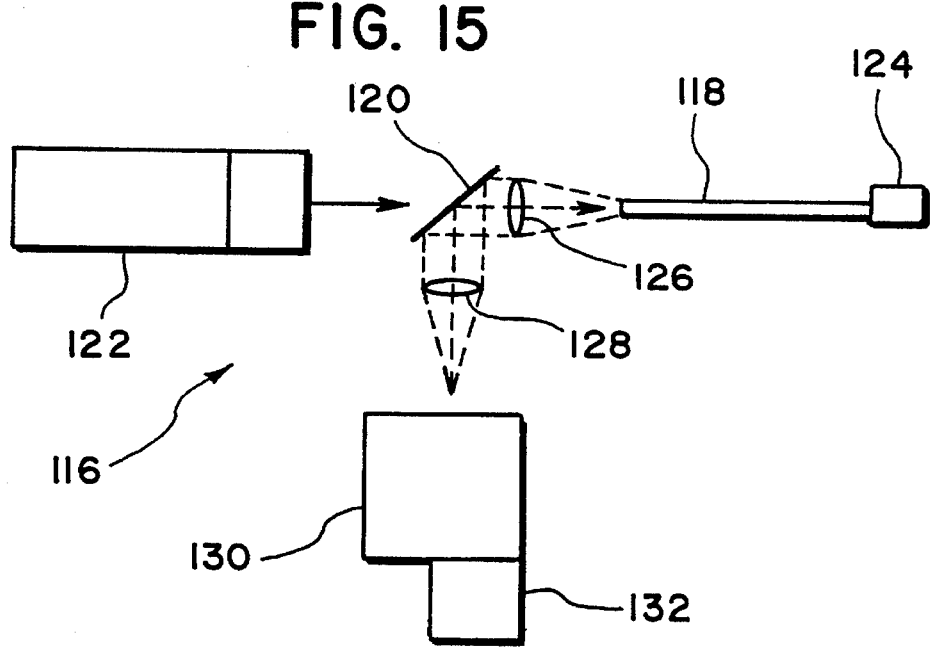
FIG. 15 is a schematic view of a photo-luminescence sensor according to another preferred embodiment of the present invention.

A variation of the FIG. 14 embodiment is shown in FIG. 15, wherein a photo-activated luminescence sensor 116 has a single-fiber 118. A mirror 120 having a central pin-hole is used to separate the excitation and emission radiation, by allowing the excitation radiation from a source 122 to pass through the mirror 120 and impinge upon a probe 124. The fluorescence from the probe 124 is collimated by a first lens 126, reflected by the mirror 120 and focused by a second lens 128 into the entrance slit of a dispersive device 130 connected to a photodetector 132.

Figure 16:
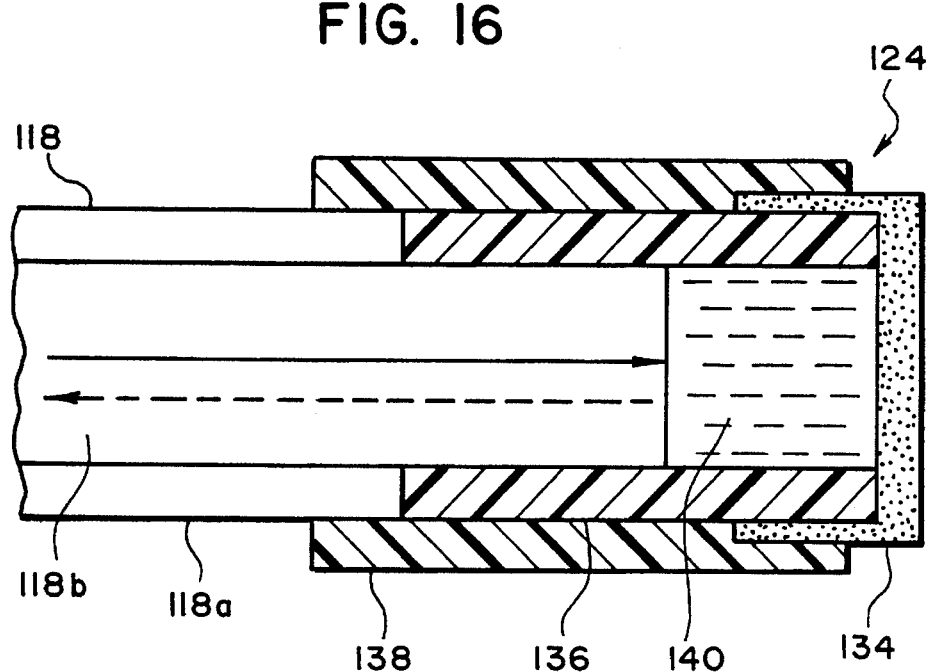
FIG. 16 is an enlarged, longitudinal sectional view of a probe according to the present invention.
Figure 17:
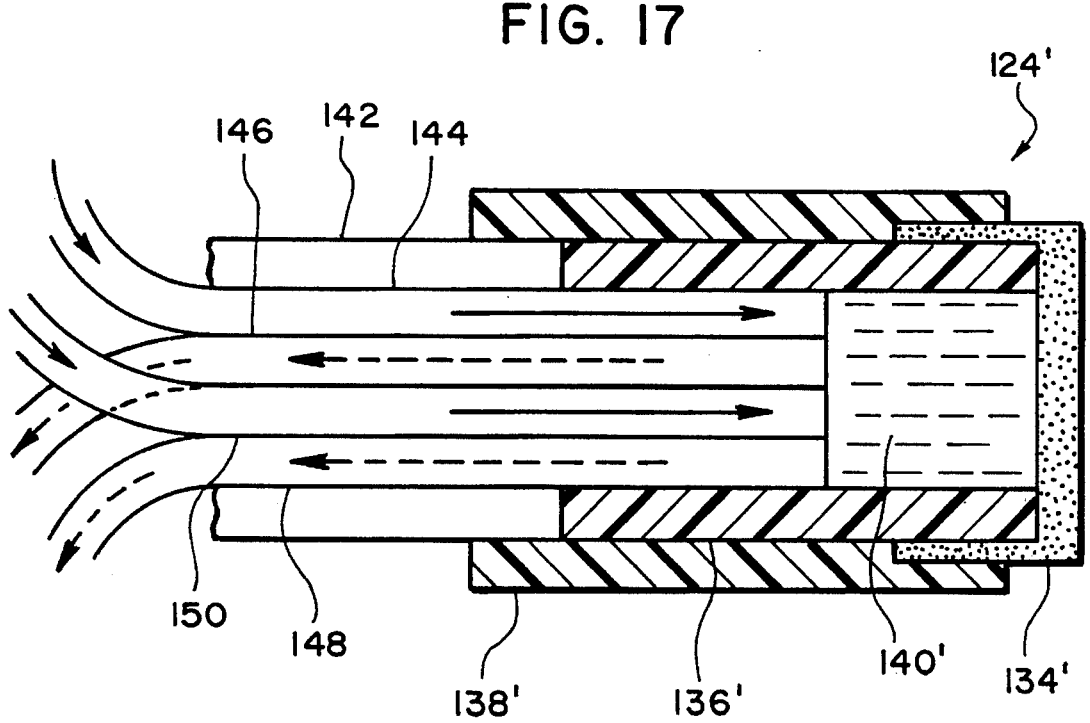
FIG. 17 is an enlarged, longitudinal sectional view of another probe according to the present invention.

The probe 124 of FIG. 15 is illustrated in greater detail in FIG. 16, and the probe 108 of FIG. 14 is illustrated in greater detail in FIG. 17. The optical fiber 118 may be a plastic-clad fused-silica fiber which includes an outer cladding 118a and an inner fiber core 118b. A membrane 134 is stretched across (or sealed on) the face of a length of plastic heat-shrink cylinder 136. The membrane may be porous TEFLON or a suitable dialysis membrane material.

The cylinder 136 is positioned tightly on the fiber core 118b. When in place, a tight seal is formed between the fiber core 118b and the plastic cylinder 136. A second heat shrink cylinder 138 is fitted over an end portion of the cladding 118a and the membrane 134 to ensure overall tightness and structural integrity of the probe 124.

A probe cavity 140 is defined as a space between the end of the core 118b, the membrane 134, and the cylindrical sidewall of the cylinder 136. The size of the probe cavity 140 is determined by the diameter of the fiberoptic diameter and the heat-shrink cylinder 136.

A probe of similar design for the bifurcated optical system is illustrated in FIG. 17, wherein the same, but primed, reference numerals are used to refer to like parts. In the bifurcated embodiment, a common cladding 142 encases multiple fiber cores 144, 146, 148, and 150. Excitation radiation is shown with the solid line directional arrows, while the emission radiation is shown with broken line directional arrows.

The fiber core may be a single core or a bundle of fibers. As an example, the plastic heat-shrink cylinder can be tapered, resulting in an inner diameter of approximately 300 µm for the microcavity which contains the photo-activator solution. The distance between the membrane and the fiber face can be adjusted to 1 mm, yielding an approximate volume of about 60 nanoliters for the microcavity. In another embodiment, the photo-activator may be embedded in a gel or sol-gel system or bound to solid particles such as microbeads contained in the microcavity (140 for FIG. 16, 140' for FIG. 17).

When the probe 124 is placed in a TCE-containing solution, the TCE molecules readily pass through the TEFLON membrane 134, diffuse into the microcavity 140 and interact with the photo-activator. The same will occur for the FIG. 17 embodiment.

Tests performed using the probes described above, using quartz capillary tubes (8 mm outer diameter, 2 mm inner diameter). The probe contained 90 µL of an ethanolic solution of DPA ($10^{-3}$ M). The analyte was introduced into the probe by adding different amounts of ethanolic solution of TCE into the capillary tube. Following UV irradiation (hv1=254 nm) of the mixture of TCE and DPA with a handheld lamp (Model UVGL-58, UVP, San Gabriel, Calif.), the photoproduct PhC is formed. When subjected to hv2 excitation at 355–360 nm, this complex PhC exhibits a broad-band luminescence emission at approximately 400–520 nm with a broad maximum band at 460–480 nm. This is illustrated in FIG. 18, wherein luminescence spectra are shown for TCE-DPA complex excitation at 355 nm, shown in the solid line "A" curve, and excitation of DPA alone at 460 nm, shown in the broken line "B" curve.

In another embodiment, the photo-activator molecules may be covalently bound to the fiber optic (such as the end of core 118b of FIG. 16, or 148 and 150 of FIG. 17).

The optimum UV irradiation (254 nm) time is 10–20 minutes. This photo-product with TCE is different in emission and excitation from that with PCB. The PCB photoproduct with DPa must be excited at wavelength<360 nm (e.g., 325 nm) whereas the TCE photo-product with DPA exhibits absorption up to 440 nm, as shown in FIG. 18. As shown in FIG. 2, the photo-activator DPA alone exhibits no significant luminescence at 400–500 nm when excited at 355–360 nm and show a spectrum with different vibrational structure than that of the TCE-DPA complex. Therefore, a vibrational technique (e.g., infrared absorption spectroscopy, Raman spectroscopy, surface-enhance Raman spectroscopy) could be used to detect TCE.

Figure 18:
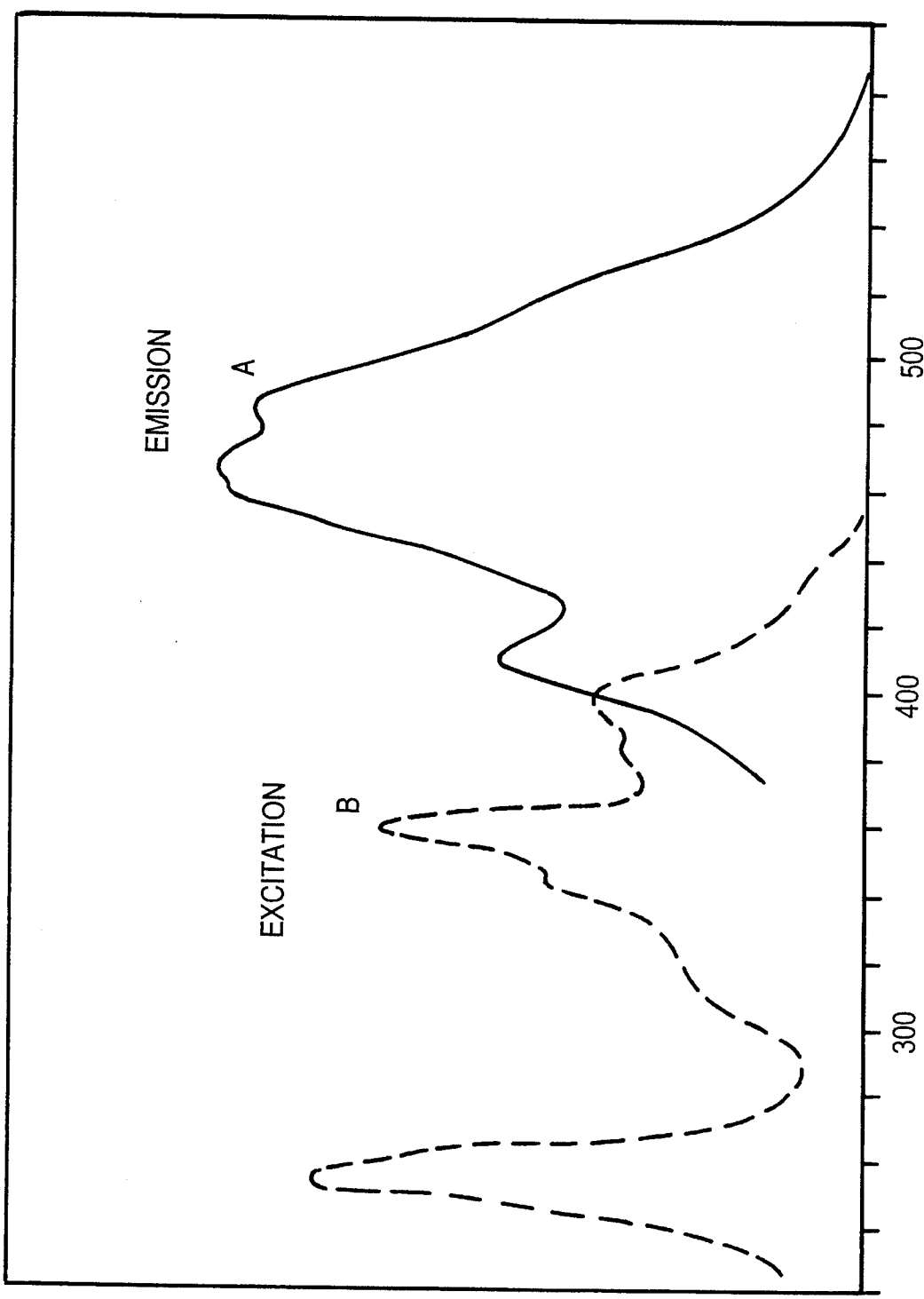
FIG. 18 are luminescence spectra, showing emission spectrum for TCE-DPA complex and excitation spectrum for DPA alone.

Comparison of FIGS. 2 and 18 also shows that the excitation spectrum (i.e., absorption spectrum) of DPA changes in absorption maxima and vibrational structure when TCE is added to DPA to form the photoproduct. This change indicates that, in addition to the luminescence change method, it is possible to use a UV-visible absorption method, infrared absorption method, light scattering method, Raman scattering method, surface-enhanced Raman method, reflection method and color change method to detect TCE.

The selectivity of the photo-luminescence sensor detection method can be further improved by using the synchronous excitation or synchronous luminescence (SL) method. The synchronous methodology consists of scanning both excitation and emission wavelengths simultaneously, by keeping a constant wavelength interval between them. The merits of the SL technique have been described previously by T. Vo-Dinh, in *Modern Fluorescence Spectroscopy*, E. L. Wehry, Ed., Plenum Press, New York, 1981).

Figure 19:
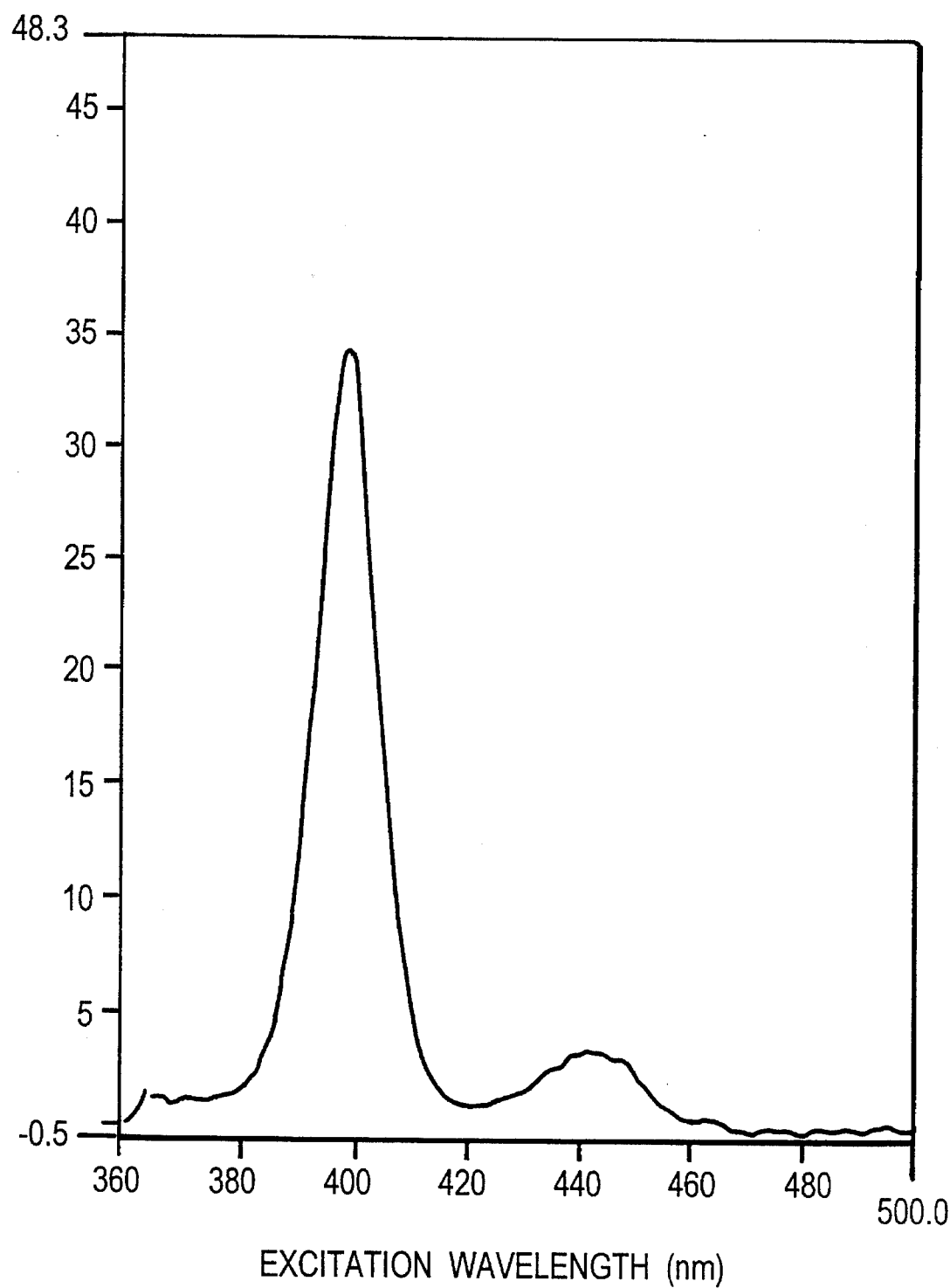
FIG. 19 is a synchronous luminescence spectrum of TCE-DPA photoproduct (10 nm wavelength emission-excitation interval)

FIG. 19 is a SL spectra of TCE-DPA photoproduct using a wavelength interval of 10 nm. The SL technique narrows the emission bands of the photoproduct, and produces an intense SL peak at about 410 nm (emission wavelength scale), thus permitting a better spectral separation of the TCE photoproducts in complex mixture (compared with the fixed-excitation spectrum in FIG. 18.

Figure 20:
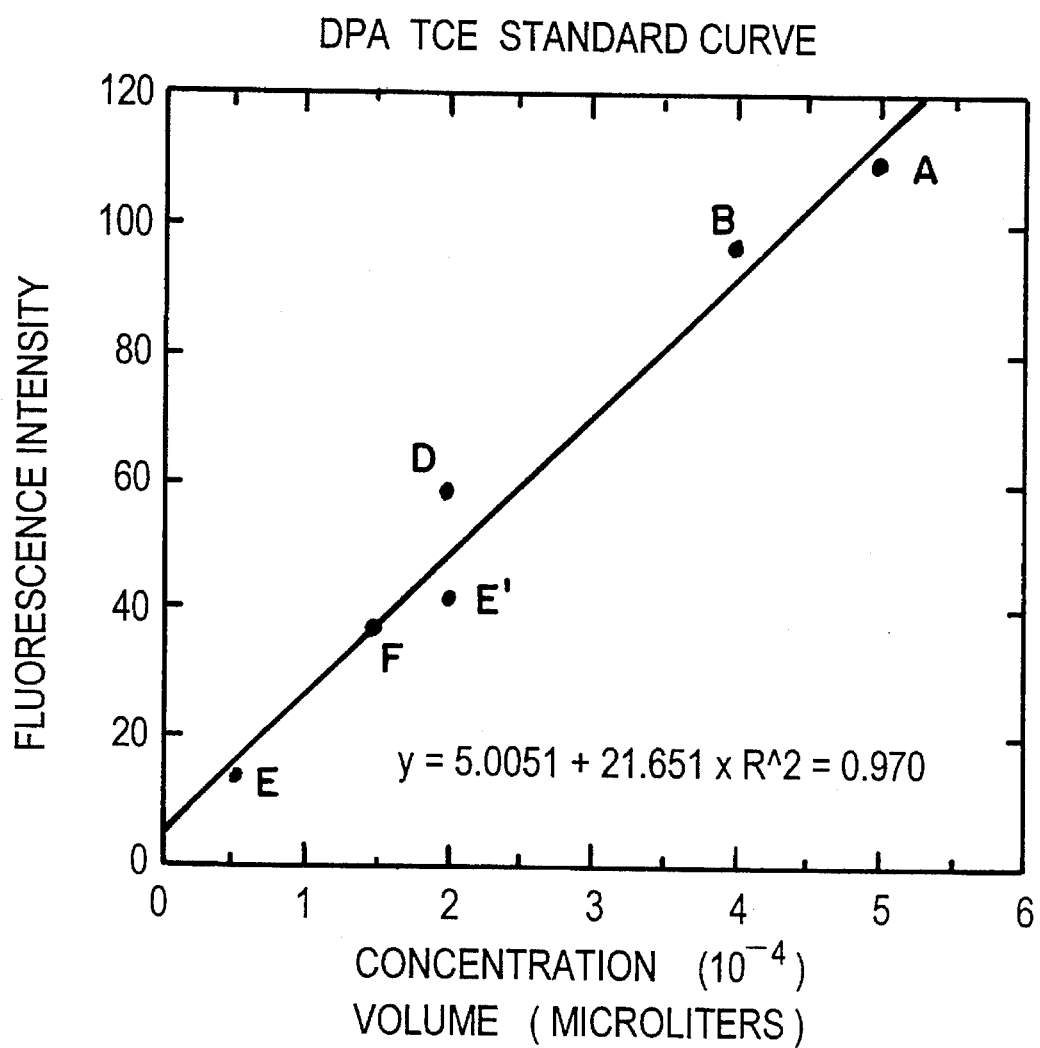
FIG. 20 is a calibration curve calculated for TCE.

In the above embodiments and examples, DPA was described as the photo-activator to illustrate the capability of the technique in determining the TCE content. FIG. 20 shows an example of a quantitative calibration curve for TCE in ethanolic solutions.

Figure 21:
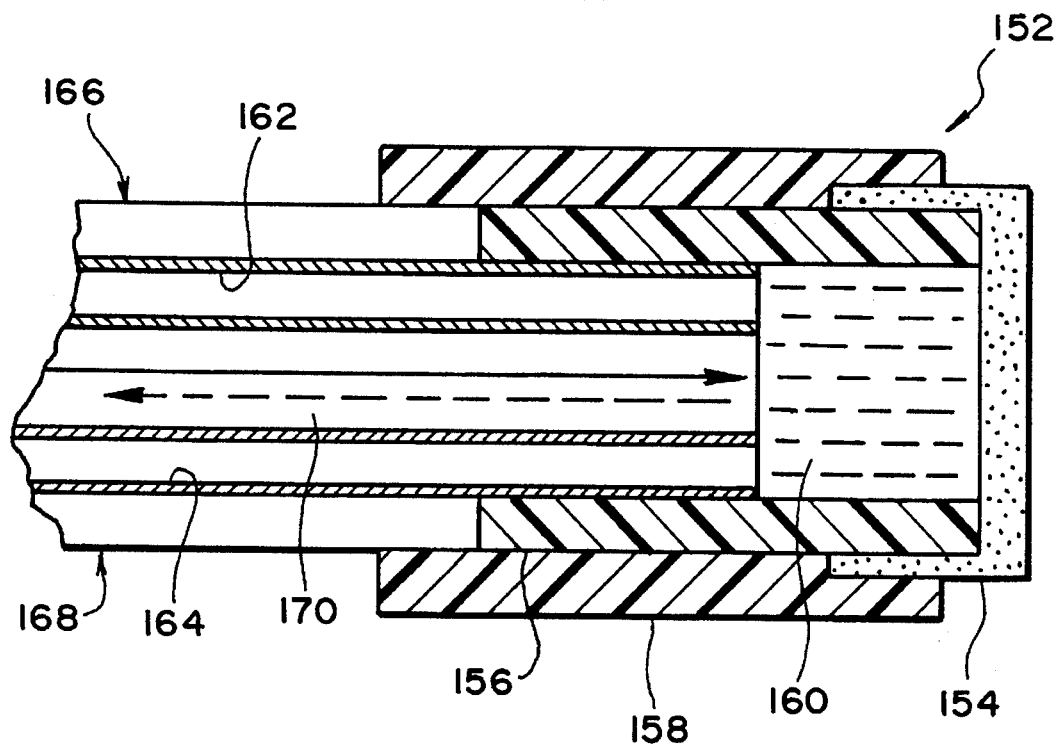
FIG. 21 is an enlarged longitudinal sectional view of another probe according to the present invention.

A further embodiment of a regenerable probe is illustrated in FIG. 21, wherein the probe 152 includes a porous membrane 154, first and second plastic cylinders 156 and 158 and a chamber 160 for containing a quantity of photo-activator. The photo-activator can be introduced prior to testing, and then removed along with photo-products after testing, using one or more conduits 162 and 164. These are in fluid communication with the chamber 160. In the illustrated embodiment a single fiber 166 is used with a single cladding 168 and single core 170, through which the excitation and emission radiation pass. The embodiment of FIG. 21 allows regeneration of the reagent system after each measurement, if desired. This system allows also rapid repetitive measurement of TCE.

Figure 22:
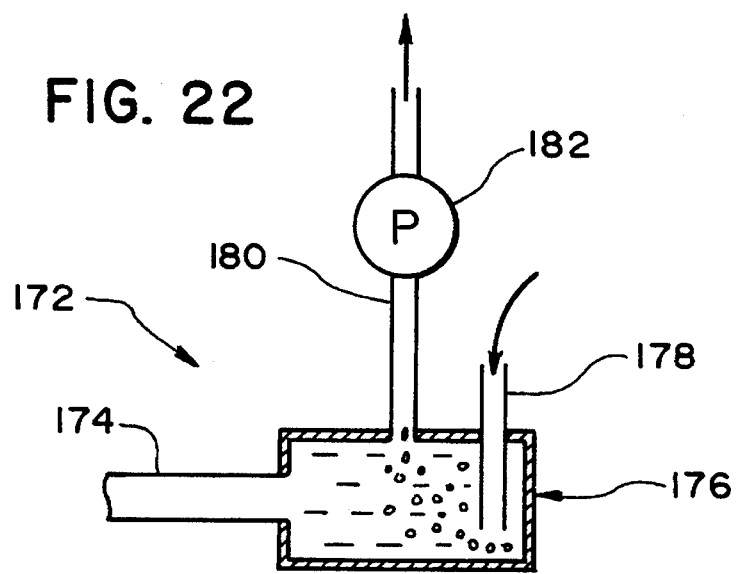
FIG. 22 is a schematic view of still another probe according to the present invention.

A further embodiment of a probe particularly suitable for gas samples is illustrated in FIG. 22. The probe 172 has an optical fiber 174 which is fed into a body 176 which has a chamber for containing a quantity of photo-activator liquid. An air inlet conduit 178 extends into the liquid and an air outlet conduit 180 is spaced therefrom. A pump 182 connected to the outlet 180 causes air to circulate through the chamber.

In the previous embodiments, the membrane can be used to monitor TCE or VOCs in the gas phase since the TCE molecules in gas samples can diffuse readily through the TEFLON membrane. The FIG. 22 embodiment achieves rapid TCE transfer into the probe by passing or bubbling the gas through the chamber containing the photo-activator in a solution that retains TCE and/or other target VOCs. The photo-activator could also be dissolved in an organic solvent that preferentially retains and concentrates TCE and VOCs from air and/or liquid samples in order to improve sensitivity and selectivity.

A portable field instrument can be used to integrate the sampling/irradiation/detection protocol for the photo-luminescence sensor instrument. The field instrument can be very simple, since it only requires three optical filters at hv1 (for photo-activation), hv2 (for excitation), and hv3 (for luminescence detection).

It is possible that different types of VOCs exhibit a maximum luminescence signal after different UV irradiation times T. It is possible to use this difference in UV irradiation time in order to selectively increase the luminescence of a certain photoproduct due to a certain type of VOCs.

The present invention can be used in many areas, including, but not limited to, environmental remediation, environmental monitoring of TCE, PCE, DCE and related VOCs, and for sensors for in-situ bioremediation of TCE, PCE, DCE and related VOCs.

The photo-luminescence sensor and methodology described above has several unique and advantageous features. First, it is a relatively simple two-step technique that combines photo-activation and excitation processes to yield measurements of TCE. Secondly, the unique probe facilitates the sensing volatile compounds that might otherwise be difficult to sense. Thirdly, the methodology allows quantitative determination of TCE and VOC content. It also provides rapid analysis and the capability of making field measurements in-situ.

The present invention is also suitable for screening samples where a rapid estimation for TCE and VOCs is required. Such screening procedures can significantly decrease the cost of environmental monitoring and remediation of TCE and VOCs contaminated sites relatively 124' can be further improved The aforementioned tests were conducted using a 254-nm line of the handheld lamp for photo-activation because it is readily available. Use of another wavelength (e.g., <254 nm) is also possible as long as it is capable of photo-activating the TCE-DPA complex.

While advantageous embodiments have been chosen to illustrate the invention, it will be understood by those skilled in the art that various changes and modifications can be made therein without departing from the scope of the invention as defined in the appended claims.

What is claimed is:

1. A method of testing for the presence of an organochloride contaminant, comprising the steps of:

exposing a probe containing a photo-activator to a sample suspected of containing the organochloride contaminant so that the organochloride, if present, and the photo-activator form a complex;

irradiating the photo-activator/contaminant complex with UV light at a first wavelength for a time sufficient to form a photo-product; and detecting the photo-product, the presence of the photo-product being indicative of the presence of the organochloride contaminant.

2. The method of claim 1, wherein the detecting step comprises irradiating the photo-product with a light of a second wavelength to cause the photo-product to luminesce, the luminescence of the photo-product complex being indicative of the presence of organochloride contaminant.

3. The method of claim 1, wherein the detecting step comprises exposing the photo-product to a scanning light having a range of wavelength and measuring absorption of the scanning light by the photo-product.

4. The method of claim 1, wherein the detecting step comprises exposing the photo-product to a scanning light having a range of wavelength and measuring reflection of the scanning light from the photo-product.

5. The method of claim 1, wherein the detecting step comprises exposing the photo-product to a scanning light having a range of wavelengths and measuring scattering of the scanning light from the photo-product.

6. The method of claim 1, wherein the detecting step comprises observing color change of the photo-product.

7. A probe for use in detecting an organochloride contaminant, comprising:

a body adapted to contain a quantity of photo-activator;

a light interface for introducing light from a source into the body; and a contaminant interface through which the organochloride contaminant, if present, passes to react with the photo-activator and thereby form a photo-product when exposed to light through the light interface.

8. A probe according to claim 7, wherein the body comprises a cylindrical member having open opposite axial ends.

9. A probe according to claim 8, wherein the light interface is at least one fiber optic fitted into one end of the cylindrical member.

10. A probe according to claim 9, wherein the contaminant interface comprises a porous membrane fitted over the other end of the cylindrical member, and being transmissive of the organochloride contaminant.

11. A probe according to claim 7, wherein the contaminant interface comprises a porous membrane fitted over the other end of the cylindrical member, and being transmissive of the organochloride contaminant.

12. A probe according to claim 7, further comprising a chamber disposed within the cylindrical member for containing the photo-activator.

13. A probe according to claim 7, further comprising means for communicating photo-activator to and from the body.

14. A probe according to claim 13, wherein the communicating means comprises at least one conduit extending into the body.

15. A probe according to claim 7, wherein the contaminant interface comprises a gas inlet and a gas outlet formed in the body.

16. A probe according to claim 15, further comprising a pump connected to one of the gas inlet and gas outlet for circulating gas through the body.

17. An apparatus for determining the presence of an organochloride contaminant, comprising:

a probe having means for containing a photo-activator and an interface through which a sample suspected of containing the organochloride contaminant is contacted so that the organochloride, if present, and the photo-activator from a complex;

means, optically coupled to the probe, for irradiating the photo-activator/contaminant complex with light at a first wavelength for a time sufficient to form a photo-product; and means, optically coupled to the probe, for detecting the photo-product, the presence of the photo-product being indicative of the presence of the organochloride contaminant.

18. An apparatus according to claim 17, wherein the irradiating means comprises a light source and a bifurcated optical fiber having a first portion communicating excitation light to the probe and a second portion communicating emission light to the detecting means.

19. An apparatus according to claim 17, wherein the irradiating means comprises a light source, a mirror disposed between the light source and the probe and having a pinhole for through which excitation light passes through to the probe, and a single optical fiber disposed between the mirror and the probe, emission light being reflected from the mirror to the detecting means.

* * * * *